US012728278B2

(12) United States Patent
Yoon et al.

(10) Patent No.: US 12,728,278 B2
(45) Date of Patent: Sep. 8, 2026

(54) METHOD AND SYSTEM FOR OPTIMIZING ELECTRODE ARRAY STRUCTURE IN ELECTROTHERAPY

(71) Applicants: FIELDCURE CO., LTD., Seoul (KR); KOREA UNIVERSITY RESEARCH AND BUSINESS FOUNDATION, Seoul (KR)

(72) Inventors: Myongguen Yoon, Gyeonggi-do (KR); Geon Oh, Seoul (KR)

(73) Assignees: FIELDCURE CO., LTD., Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 334 days.

(21) Appl. No.: 18/568,748

(22) PCT Filed: May 16, 2022

(86) PCT No.: PCT/KR2022/006976
§ 371 (c)(1),
(2) Date: Dec. 8, 2023

(87) PCT Pub. No.: WO2022/265232
PCT Pub. Date: Dec. 22, 2022

(65) Prior Publication Data

US 2024/0261585 A1 Aug. 8, 2024

(30) Foreign Application Priority Data

Jun. 14, 2021 (KR) ........................ 10-2021-0076738

(51) Int. Cl.
*A61N 1/40* (2006.01)

(52) U.S. Cl.
CPC ..................................... *A61N 1/40* (2013.01)

(58) Field of Classification Search
CPC .......... A61N 1/04; A61N 1/0476; A61N 1/08; A61N 1/40
See application file for complete search history.

(56) References Cited

U.S. PATENT DOCUMENTS 8,764,675 B2 7/2014 Palti
2012/0101398 A1* 4/2012 Ramanathan .......... A61B 5/339 600/523

(Continued)

FOREIGN PATENT DOCUMENTS

JP 2012-508079 4/2012
KR 10-2012-0017356 2/2012

(Continued)

OTHER PUBLICATIONS

International Search Report mailed Sep. 6, 2022 for PCT/KR2022/006976.

(Continued)

*Primary Examiner* — Tigist S Demie

(57) ABSTRACT

A method of optimizing an electrode array structure in electrotherapy, the method comprising: obtaining information on a region-of-interest (ROI) and critical organs from input patient data; setting an overall shape and an overall area of an electrode array based on the obtained information on the region-of-interest (ROI) and critical organs; setting an area ratio occupied by a plurality of unit electrodes constituting the electrode array to the overall area of the electrode array; repeatedly performing the setting of the overall shape and the overall area and/or the setting of the area ratio until an electric field transmitted to the region-of-interest (ROI) and the critical organs is optimized; and deriving a customized electrode array structure in which the electric field is optimized; is provided.

10 Claims, 10 Drawing Sheets

210

211 patient information acquisition unit

212 Electrode setting unit 213 electric field simulation unit

(56) References Cited

U.S. PATENT DOCUMENTS

2019/0355476 A1 11/2019 Palti
2021/0228896 A1* 7/2021 Yoon .................... A61N 1/3603

FOREIGN PATENT DOCUMENTS

KR 10-2020-0004228 1/2020
KR 10-2021-0034620 3/2021

OTHER PUBLICATIONS

K. Heimrath et al, Transcranial direct current stimulation (tDCS) over the auditory cortex modulates GABA and glutamate: a 7 T MR-spectroscopy study, Scientific Report, 10, 20111 (2020).
Eilon D. Kirson et al, Disruption of cancer cell replication by alternating electric fields, Cancer Research, 64, 3288-3295 (2004).
Miklos Pless, Uri Weinberg, Tumor treating fields: concept, evidence, future, Expert Opinion, 20(8), 1099-1106 (2011).
Stupp et al, Effect of Tumor-Treating Fields Plus Maintenance Temozolomide vs Maintenance Temozolomide Alone on Survival in Patients With Glioblastoma: A Randomized Clinical Trial, Journal of the American Medical Association, 318(23), 2306-2316 (2017).
Eilon D. Kirson et al. Alternating electric fields (TTFields) inhibit metastatic spread of solid tumors to the lungs, Clin Exp Metastasis 26, 633-640 (2009).
Novocure Corporate Presentation (https://3sj0u94bgxp33grbzlfkt62h-wpengine.netdna-ssl.com/wp-content/uploads/201 9/05/201905_NVCR_Corporate_Presentation_vFF.pdf).
Eilon D. Kirson et al, Alternating electric fields arrest cell proliferation in animal tumor models and human brain tumors, PNAS, 104(24), 10152-10157 (2007).
Yunhui Jo et al, Effectiveness of a Fractionated Therapy Scheme in Tumor Treating Fields Therapy, Technology in Cancer Research & Treatment, 18, 1-10 (2019).
Elijah J. Mun et al, Tumor-Treating Fields: A Fourth Modality in Cancer Treatment, Clinical Cancer Research, 24(2), 266-275, 2018.

* cited by examiner

Surface area of electrode : 14.5 $cm^2$

Surface area of electrode : 25.8 $cm^2$

Surface area of electrode : 58.1 $cm^2$

Surface area of electrode : 103.29 $cm^2$

Surface area of electrode : 161.4 $cm^2$

Surface area of electrode : 207.3 $cm^2$

Total area
of electrode array (b-4)

Area of
individual electrode

ROI

OAR

Case 1

Case 2

Case 4

METHOD AND SYSTEM FOR OPTIMIZING ELECTRODE ARRAY STRUCTURE IN ELECTROTHERAPY

This application claims the priority of Korean Patent Application No. 10-2021-0076738, filed on Jun. 14, 2021 in the KIPO (Korean Intellectual Property Office), the disclosure of which is incorporated herein entirely by reference. Further, this application is the National Stage application of International Application No. PCT/KR2022/006976, filed on May 16, 2022, which designates the United States and was published in Korean. Each of these applications is hereby incorporated by reference in their entirety into the present application.

TECHNICAL FIELD

The present application relates to a method and a system for optimizing an electrode array structure in electrotherapy, more specifically, to a method and a system for optimizing an electrode array structure in electrotherapy, which are capable of setting a structure of an electrode array in a way to apply an maximum electric field (or a current for generating the electric field) to a Region-of-interest (ROI) in a human body and minimum electric field to an Organ-at-risk (OAR) by adjusting the overall area or shape of electrode or array and/or an area ratio occupied by a plurality of unit electrodes constituting the electrode array to the overall area of the electrode.

BACKGROUND ART

The electrotherapy uses electric energy for therapeutic purposes, imparts an electric field to the human body using an electrode, and uses a heating effect such as an electric bath (heat therapy), an ultrashort wave therapy, and the like, in addition to the electrostimulation therapy for various neuro-paralysis, and cancer therapy using an AC voltage (see non-patent references 1-6).

In general, electrotherapy in which an electrode is attached to the skin and then a voltage is applied to the human body uses an electric field (or a current generated by the electric field) generated in the human body by the applied voltage.

In one example, the effect of the electric field treatment on cancer cells varies depending on the intensity of the electric field applied to the tissue. In detail, as the intensity of the electric field increases, the effect of inhibiting apoptosis and division of cancer cells increases, and thus the intensity of the electric field is proportional to the effect of apoptosis (see non-patent references 7 and 8). In the case of the currently commercialized electric field cancer treatment system, the intensity of the electric field is treated by applying the maximum electric field to the skin to such extent that there are no side effects. However, it is problem that conventional treatment using an electrode array with a uniform shape and size does not consider the size and shape of the region-of-interest (ROI) and the location of the region-of-interest (ROI) in the human body at all, and as a result, inefficient treatment results may occur be caused because the electric field is not sufficiently applied to the region-of-interest (ROI) or the electric field is unnecessarily applied to surrounding critical organs as well as the region-of-interest (ROI) (see non-patent reference 9 and patent reference 1).

Thus, to minimize side effects while maximizing treatment effects in electrotherapy with an electrode array, a technology for customizing electrotherapy to each individual patient, considering the size and shape of the region-of-interest (ROI) and the position of the region-of-interest (ROI) in the human body is required.

PRIOR ART DOCUMENT (Patent reference 1) U.S. Registered Patent U.S. Pat. No. 8,764,675 B2, Jul. 1, 2014. Registered.

(Non-Patent reference 1) K. Heimrath et al, Transcranial direct current stimulation (tDCS) over the auditory cortex modulates GABA and glutamate: a 7 T MR-spectroscopy study, Scientific Report, 10, 20111 (2020).

(Non-Patent reference 2) Eilon D. Kirson et al, Disruption of cancer cell replication by alternating electric fields, Cancer Research, 64, 3288-3295 (2004).

(Non-Patent reference 3) Miklos Pless, Uri Weinberg, Tumor treating fields: concept, evidence, future, Expert Opinion, 20(8), 1099-1106 (2011).

(Non-Patent reference 4) Stupp et al, Effect of Tumor-Treating Fields Plus Maintenance Temozolomide vs Maintenance Temozolomide Alone on Survival in Patients With Glioblastoma: A Randomized Clinical Trial, Journal of the American Medical Association, 318 (23), 2306-2316 (2017).

(Non-Patent reference 5) Eilon D. Kirson et al. Alternating electric fields (TTFields) inhibit metastatic spread of solid tumors to the lungs, Clin Exp Metastasis 26, 633-640 (2009).

(Non-Patent reference 6) Novocure Corporation Presentation (https://3sj0u94bgxp33grbz1fkt62h-wpengine.netdna-ssl.com/wp-content/uploads/2019/05/201905_NVCR_Corporate_Presentation_vFF.pdf).

(Non-Patent reference 7) Eilon D. Kirson et al, Alternating electric fields arrest cell proliferation in animal tumor models and human brain tumors, PNAS, 104 (24), 10152-10157 (2007).

(Non-Patent reference 8) Yunhui Jo et al, Effectiveness of a Fractionated Therapy Scheme in Tumor Treating Fields Therapy, Technology in Cancer Research & Treatment, 18, 1-10 (2019).

(Non-Patent reference 9) Elijah J. Mun et al, Tumor-Treating Fields: A Fourth Modality in Cancer Treatment, Clinical Cancer Research, 24(2), 266-275, 2018.

DISCLOSURE OF THE INVENTION

Technical Problem

The present disclosure is directed to providing a method for reducing inefficiency of electric field therapy, which occurs by using electrode arrays with the same shape and size without considering the size, shape, and location of the region-of-interest (ROI) in the body of a patient while preventing various side effects that may occur in the electric field therapy process in advance, and optimizing the intensity of the electric field delivered to the region-of-interest (ROI).

Technical Solution

The present disclosure provides a method of optimizing an electrode array structure in electrotherapy, the method comprising: obtaining information on a region-of-interest (ROI) and critical organs from input patient data; setting an overall shape and an overall area of an electrode array based on the obtained information on the region-of-interest (ROI) and critical organs; setting an area ratio occupied by a plurality of unit electrodes constituting the electrode array to the overall area of the electrode array; repeatedly performing the setting of the overall shape and the overall area and/or the setting of the area ratio until an electric field transmitted to the region-of-interest (ROI) and the critical organs is optimized; and deriving a customized electrode array structure in which the electric field is optimized.

In an exemplary embodiment of the present disclosure, obtaining information on a region-of-interest (ROI) and critical organs may comprise dividing the region-of-interest (ROI) and the critical organ from the input medical image of the patient.

In an exemplary embodiment of the present disclosure, the information on a region-of-interest (ROI) may contain information about a size, a shape, and an internal depth of the body of the patient, and the information on critical organ contains information about a shape and a location of the critical organ.

In an exemplary embodiment of the present disclosure, the setting of the overall shape and the overall area may comprise setting the overall shape of the electrode array based on a shape of a region-of-interest (ROI) from a viewpoint of the skin to which the electrode is attached.

In an exemplary embodiment of the present disclosure, the setting of the overall shape and the overall area may comprise setting the overall shape of the electrode array by additionally considering the shape and position of the critical organ.

In an exemplary embodiment of the present disclosure, the overall area of the electrode array may be a saturation critical area, which is an area where the average intensity of the electric field transmitted to the region-of-interest (ROI) starts to be constant, based on the set overall shape of the electrode array.

In an exemplary embodiment of the present disclosure, the saturation critical area is calculated based on the following Equation.

A saturation critical $$\text{A saturation critical area} = \left(\text{a minimum value among } A \text{ values making } \frac{dI}{dA} \cong 0\right),$$

where I is average intensity of an electric field transmitted to the region-of-interest, and A is an entire area of the electrode array as a feature.

In an exemplary embodiment of the present disclosure, the saturation critical area may be calculated by considering the size of the region-of-interest (ROI) and the depth of the body.

In an exemplary embodiment of the present disclosure, the area ratio may be set so that the intensity of the electric field is equal to or greater than the intensity of the electric field that can maximize the clinical treatment effect with reference to correlation information between the area ratio of the electrode array and the intensity of the electric field transferred to the region-of-interest.

In an exemplary embodiment of the present disclosure, the repeatedly performing the setting of the overall shape, the overall area and the setting of the area ratio may comprise simulating an electric field transmitted to the region-of-interest (ROI) and the critical organ according to the ratio and the overall shape previously set, and repeatedly changing any of the overall shape, the overall area and the setting of the area ratio until the electric field transmitted to the region-of-interest (ROI) and the critical organ satisfies a predetermined criterion from the simulation results.

In an exemplary embodiment of the present disclosure, deriving a customized electrode array structure can be implemented by customizing electrode array structure or by selectively applying a voltage to only a unit electrode corresponding to the overall shape of the electrode array while using an electrode array template having a predetermined structure.

The present disclosure also provides a system for optimizing an electrode array structure in electrotherapy, the system comprising: a patient information acquisition unit configured to acquire information on a region-of-interest (ROI) and a critical organ from input patient data; an electrode array structure setting unit configured to set variables of an electrode array that determines an electrode array structure based on the information on the region-of-interest (ROI) and the critical organ, and derive a customized electrode array structure that optimizes an electric field delivered to the region-of-interest (ROI) and the critical organ based on electric field simulation results; and an electric field simulation unit configured to simulate the electric field delivered to the region-of-interest (ROI) and the critical organ according to the variables of the electrode array set by the electrode array structure setting unit.

In an exemplary embodiment of the present disclosure, the variables of the electrode array may include an entire shape and an entire area of the electrode array, and a ratio of an area occupied by a plurality of unit electrodes constituting the electrode array to the entire area of the electrode array.

Advantageous Effects

According to an embodiment of the present invention, by using a customized electrode array in which the ratio of the overall area and shape of the electrode array and the area occupied by unit electrodes to the overall area of the electrode array are adjusted based on a distance from the electrode to the region-of-interest, it is possible to perform a treatment such that the inefficiency of a treatment effect generated during an electrical treatment is reduced, and an electric field required for the treatment is maximally delivered to the region-of-interest (ROI) and at the same time, the electric field is minimally delivered to a surrounding normal tissue.

Therefore, the present invention can solve the problems of conventional treatment methods using an electrode array with a uniform shape and size and is able to expect more practical and effective clinical results.

The effects of the present invention are not limited to the effects mentioned above, and other effects not mentioned herein will be clearly understood by those skilled in the art from the following description.

BRIEF DESCRIPTION OF THE DRAWINGS

FIG. 16 is a graph illustrating the intensity of an electric field applied to the region-of-interest (ROI) and the critical organ with respect to each case illustrated in FIG. 15.

FIG. 17 is a diagram illustrating an example in which a region-of-interest (ROI) and a critical organ are assumed in a human body phantom according to another embodiment of the present invention.

BEST MODE FOR CARRYING OUT THE INVENTION

Figure 1:
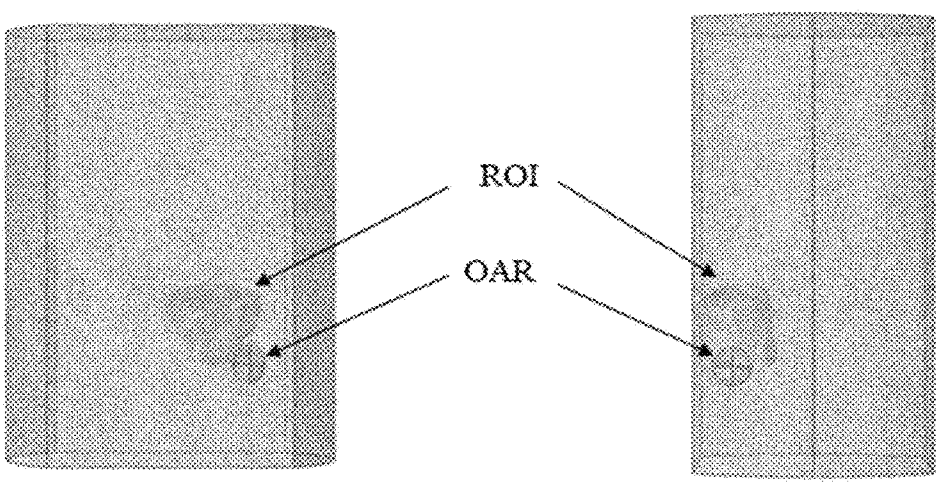
FIG. 1 is a diagram illustrating an example in which a virtual region-of-interest (ROI) and a critical organ are assumed in a human body phantom/

The present disclosure can be modified variously and may have various exemplary embodiments. Hereinafter, specific exemplary embodiments will be illustrated in the drawings and described in detail. However, it is not intended to limit the present disclosure to the specific exemplary embodiments and it should be understood that the present disclosure includes all modifications, equivalents and substitutes included in the idea and technical scope of the present disclosure. When describing the present disclosure, a detailed description of the related known technology may be omitted if it is judged that it may obscure the gist of the present disclosure.

In general, since the allowable current density of the skin surface is 30 mA/cm2 or less in the electrotherapy, the electric field simulation was performed based on the time when the voltage was applied so that the current density of the skin surface is 30 mA/cm2 or less in the following examples (see non-patent reference 7).

Figure 2:
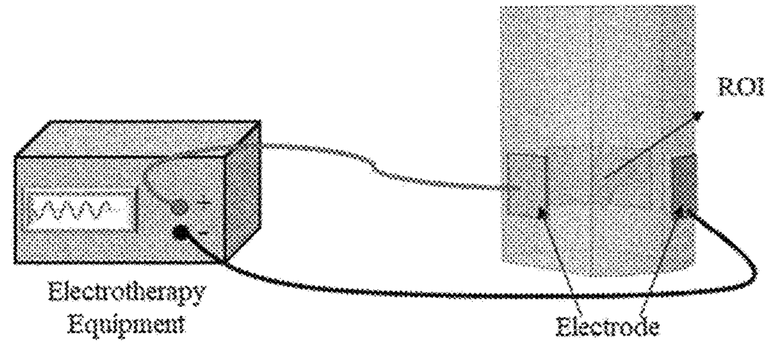
FIG. 2 is a diagram illustrating an example in which an electric field is applied to a region-of-interest (ROI) in the human body phantom illustrated in FIG. 1 by using an electrotherapy device.
Figure 3:
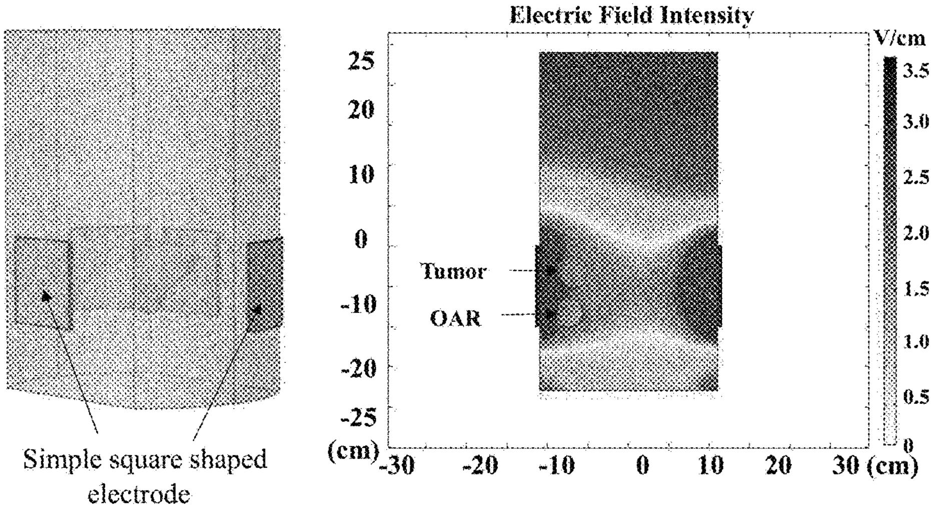
FIG. 3 is a diagram illustrating the intensity of an electric field applied to the region-of-interest (ROI) and the critical organ when a simple quadrangular-shaped electrode is used.
Figure 4:
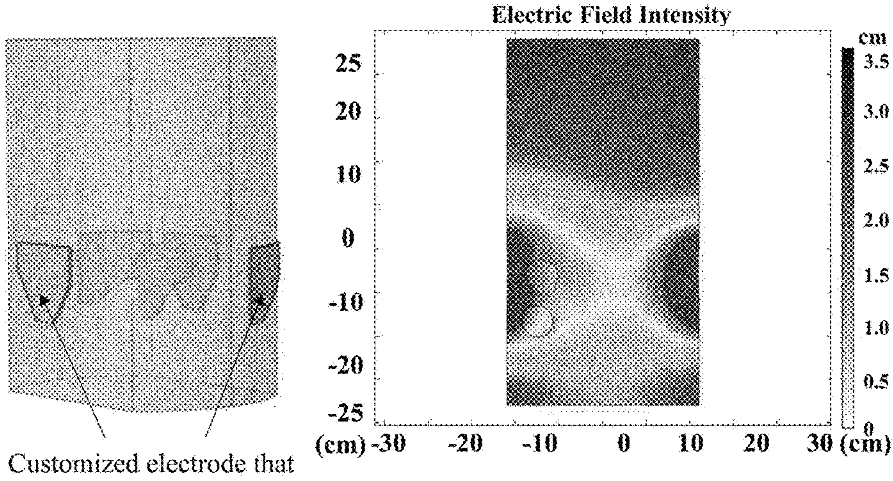
FIG. 4 is a diagram illustrating the intensity of an electric field applied to the region-of-interest (ROI) and the critical organ when a customized electrode considering the shape of the region-of-interest (ROI) is used.

FIG. 1 is a diagram illustrating an example in which a virtual region-of-interest (ROI) and a critical organ are assumed in a human body phantom, FIG. 2 is a diagram illustrating an example in which an electric field is applied to a region-of-interest (ROI) in the human body phantom illustrated in FIG. 1 by using an electrotherapy device, FIG. 3 is a diagram illustrating the intensity of an electric field applied to the region-of-interest (ROI) and the critical organ when a simple quadrangular-shaped electrode is used, and FIG. 4 is a diagram illustrating the intensity of an electric field applied to the region-of-interest (ROI) and the critical organ when a customized electrode considering the shape of the region-of-interest (ROI) is used.

As shown in FIG. 1, a virtual region-of-interest (ROI) and an organ-at-risk (OAR) are assumed in the human phantom, and as shown in FIG. 2, an electrode is attached around the region-of-interest (ROI) of the human phantom and an electric field may be applied using electrotherapy equipment.

As shown in FIG. 3, when a simple square shaped electrode is used, average intensities of electric fields transmitted to the region-of-interest (ROI) and the organ-at-risk (OAR) are 3.38 V/cm and 3.24 V/cm, respectively, and it can be seen that the intensities of electric fields are almost the same.

On the other hand, as shown in FIG. 4, when a customized electrode(s) that conforms to the shape of the ROI is(are) used, the average intensities of the electric fields transmitted to the region-of-interest (ROI) and the organ-at-risk (OAR) are 3.39 V/cm and 2.38 V/cm, respectively.

In other words, it can be seen that the case of using an electrode (FIG. 4) having a shape conforming to the shape of the ROI seen from the skin to which the electrode is attached (that is, the viewpoint of the electrode or electrode-eye-view) can minimize the electric field transmitted to the surrounding normal tissue while transmitting a sufficient electric field to the region-of-interest (ROI), as compared with the case of using an electrode with a predetermined same shape (refer to FIG. 3).

Figure 5:
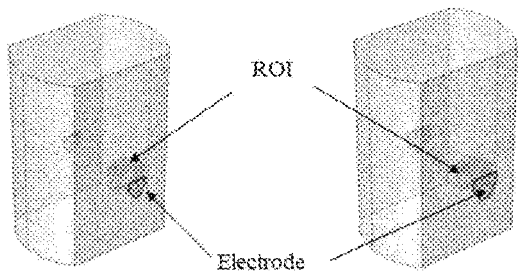
FIG. 5 is a diagram illustrating an example in which the shape of the electrode is the same and the area of the electrode is variously changed.
Figure 5:
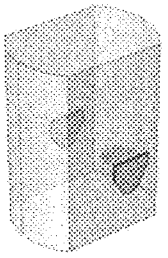
Figure 5:
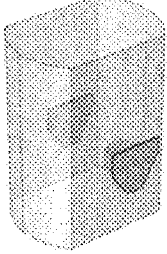
Figure 5:
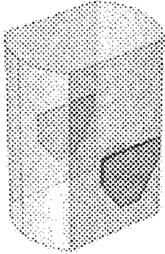
Figure 5:
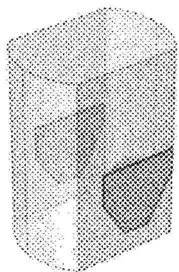
Figure 6:
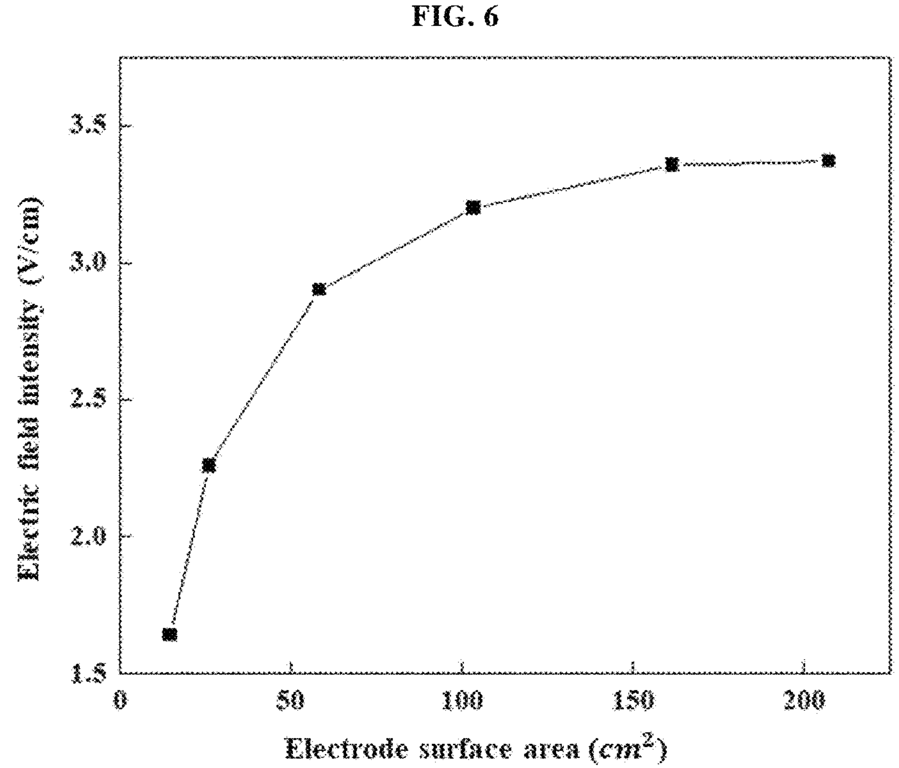
FIG. 6 is a graph illustrating a correlation between the area of the electrode and the average intensity of the electric field applied to the region-of-interest (ROI) when the electrodes having different areas illustrated in FIG. 5 are used.

FIG. 5 is a diagram illustrating an example in which the shape of the electrode is the same and the area of the electrode is variously changed, and FIG. 6 is a graph illustrating a correlation between the area of the electrode and the average intensity of the electric field applied to the region-of-interest (ROI) when the electrodes having different areas illustrated in FIG. 5 are used.

Referring to FIG. 5, the electrodes with the same shape cover different areas of 14.5 $cm^2$, 25.8 $cm^2$, 58.1 $cm^2$, 103.29 $cm^2$, 161.4 $cm^2$, and 207.3 $cm^2$, respectively.

Referring to FIG. 6, after applying voltage to the electrodes, the average intensity of the electric field transmitted to the region-of-interest (ROI) increases in proportion to the overall area of electrodes, but over a certain area (hereinafter, saturation critical area), the average intensity of the electric field transmitted to the region-of-interest (ROI) becomes substantially constant. Hereinafter, an area where the average intensity of the electric field transmitted to the region-of-interest (ROI) starts to be substantially constant may be defined as a saturation critical area, and the saturation critical area may be defined as Equation 1 below.

$$\text{Critical area} = \left(\text{Minimum of } A \text{ value making } \frac{dI}{dA} \cong 0\right) \quad \text{[Equation 1]}$$

where, I is the average intensity of the electric field transmitted to the region-of-interest (ROI), and A is the overall area of the electrode.

In other words, the saturation critical area can be interpreted as the minimum area where the electric field intensity does not substantially increase even as the area of the electrode increases.

The critical area of the electrode calculated from Equation 1 helps the intensity of the electric field transmitted to the region-of-interest (ROI) to maximize, and at the same time, avoiding using an unnecessarily large electrode.

Figure 7:
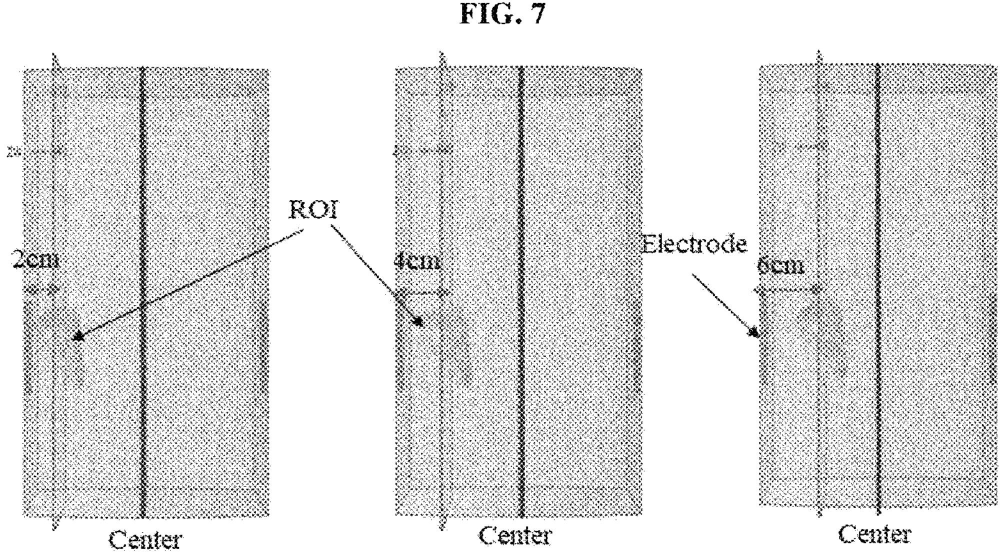
FIG. 7 is a diagram illustrating an example of a case in which the body depth of the ROI is variously changed.
Figure 8:
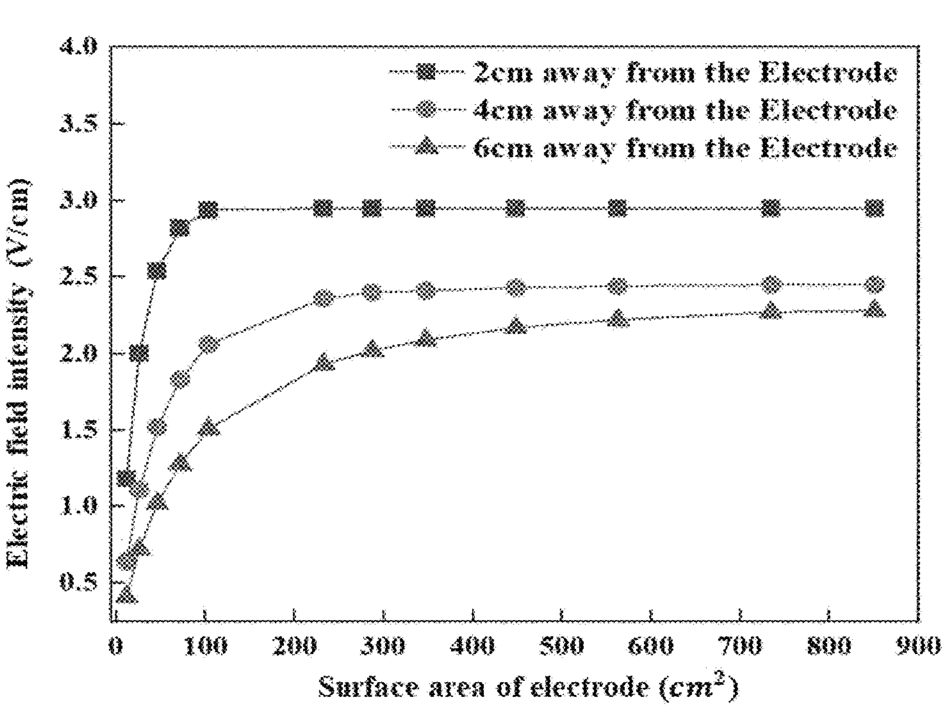
FIG. 8 is a graph illustrating a correlation between the area of the electrode and the average intensity of the electric field applied to the ROI when the electric field is applied to the ROI illustrated in FIG. 7.

FIG. 7 is a diagram illustrating an example of a case in which the body depth of the ROI is variously changed, and FIG. 8 is a graph illustrating a correlation between the area of the electrode and the average intensity of the electric field applied to the region-of-interest (ROI) when the electric field is applied to the ROI as illustrated in FIG. 7.

As shown in FIG. 7, it is assumed that the depth of the region-of-interest (ROI) in the human body phantom, that is, the distance between the region-of-interest (ROI) and the electrode is 2 cm, 4 cm, and 6 cm, respectively.

Referring to FIG. 8, as shown in FIG. 5, when a voltage is applied to the phantom human body shown in FIG. 7 while changing the overall area of the electrode, critical area increases as the distance from the electrode to the ROI increases even though the region-of-interest (ROI) has the same size.

Considering the above description with reference to FIGS. 1 to 8, it can be seen that the size and shape of the region-of-interest (ROI) viewed from the viewpoint of the electrode and the distance between the electrode and the region-of-interest (ROI) should be considered in order to set(determine) the overall area of the electrode, and the overall area and shape of the electrode in which the three variables are considered should be set to a value close to the critical area, which is an area in which the intensity of the electric field begins to saturate.

Figure 9:
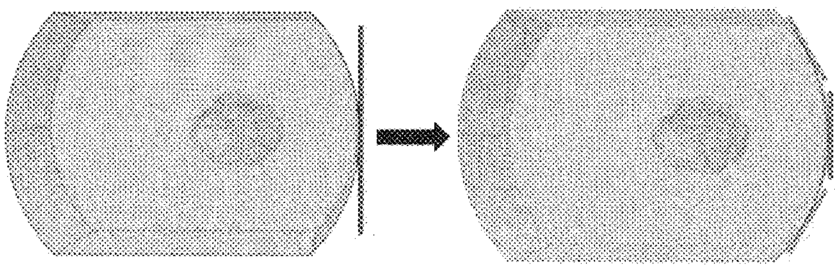
FIG. 9 is a diagram illustrating a comparison between a case in which a single flat panel electrode is attached to a bent portion and a case in which an electrode array including a plurality of unit electrodes is attached to the bent portion in the human model phantom illustrated in FIG. 1.
Figure 10:
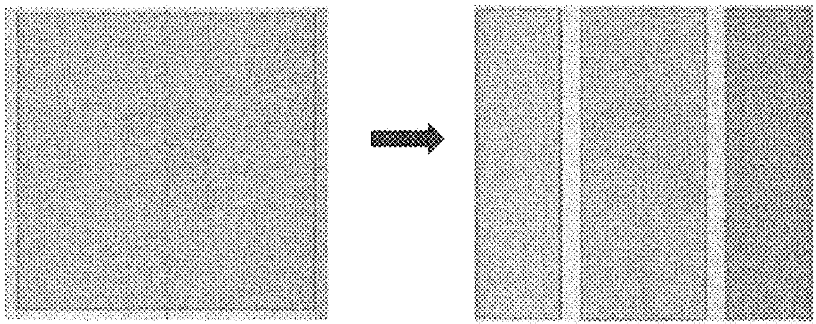
FIG. 10 is a diagram illustrating a case in which the single flat panel electrode and the electrode array illustrated in FIG. 9 are viewed in an electrode attachment direction.

FIG. 9 is a diagram illustrating a comparison between a case in which a single flat panel electrode is attached to a bent portion and a case in which an electrode array including a plurality of unit electrodes is attached to the bent portion in the human model phantom illustrated in FIG. 1, and FIG. 10 is a diagram illustrating a case in which the single flat panel electrode and the electrode array illustrated in FIG. 9 are viewed in an electrode attachment direction.

As shown on the left side of FIG. 9, when a single flat panel electrode is attached to a bent portion, the electrode is not properly attached, and an empty space is formed between the electrode and the bent portion. On the other hand, as shown in the right side of FIG. 9, it can be seen that when an electrode array including three-unit electrodes is attached instead of a single flat panel electrode, the empty space is reduced, and the electrode is easily attached to a bent portion.

FIG. 10 illustrates a case in which the single flat panel electrode and the electrode array illustrated in FIG. 9 are viewed in an electrode attachment direction.

Referring to FIGS. 9 and 10, the body of a patient to be treated with electrotherapy has different curves, and there is a limitation in attaching a single flat panel electrode to the curved body. In addition, since the electrode itself is very large when the electrotherapy is performed using a single flat panel electrode, side effects such as an electric shock that may occur when a current is leaked to only one side of a patient who is receiving the therapy, and a breaking of the electrode that may occur because of the movement of the patient.

However, when an electrode array including a plurality of unit electrodes is used, the unit electrodes may be attached to a curved portion as well as a flat portion in an effective and customized manner. Furthermore, since small sized unit electrodes can be individually controlled, side effects such as current leakage and electrode breakage can be prevented in advance.

Figure 11:
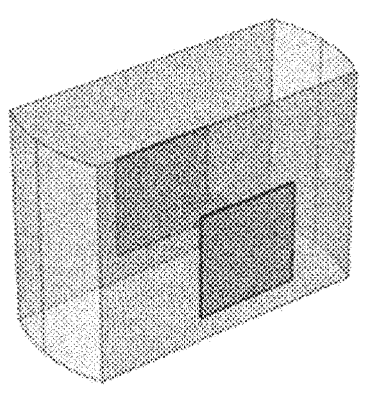
FIG. 11 is a diagram illustrating an example in which the overall area of an electrode array is set according to an embodiment of the present disclosure.
Figure 11:
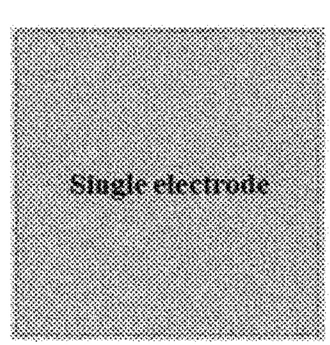
Figure 12:
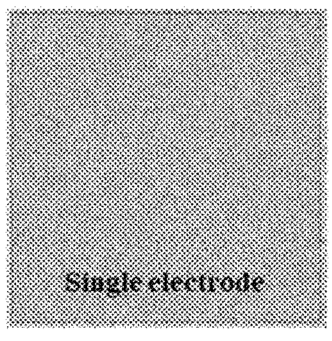
FIG. 12 is a diagram illustrating an example in which the overall area of the electrode array illustrated in FIG. 11 is maintained and an area ratio occupied by a plurality of unit (or individual) electrodes is variously changed.
Figure 12:
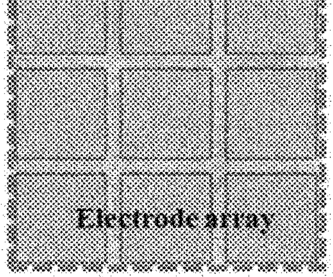
Figure 12:
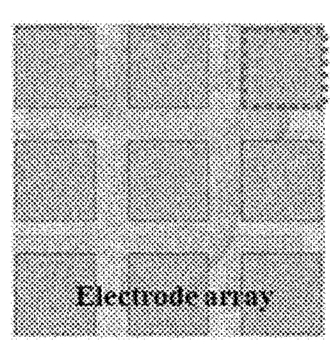
Figure 12:
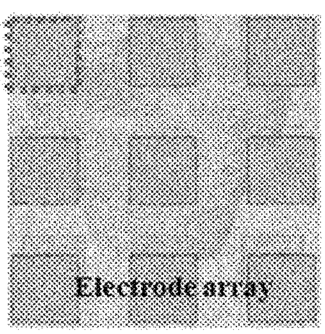
Figure 12:
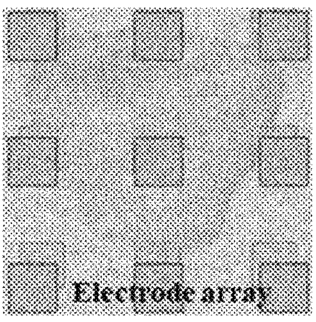
Figure 12:
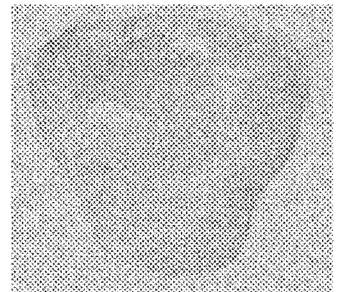
Figures 13, 14:
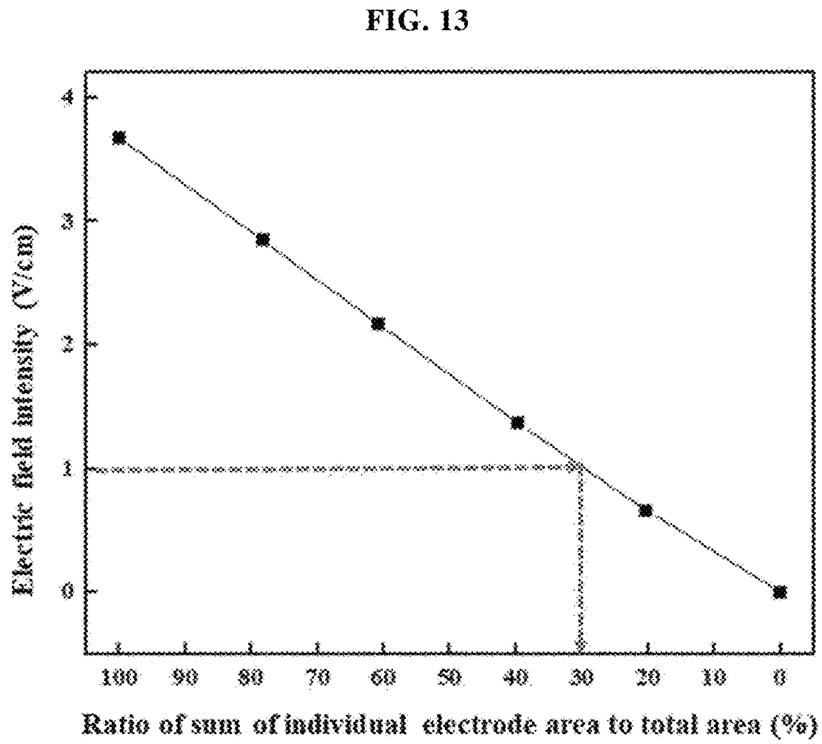
FIG. 13 is a graph illustrating a correlation between an area ratio and an average intensity of an electric field applied to a region-of-interest (ROI) when an electric field is applied using electrode arrays having different area ratios illustrated in FIG. 12.
FIG. 14 is a diagram illustrating an example in which a region-of-interest (ROI) and a critical organ are assumed in a human body model phantom according to an embodiment of the present invention.

FIG. 11 is a diagram illustrating an example in which the overall area of an electrode array is set according to an embodiment of the present disclosure, FIG. 12 is a diagram illustrating an example in which the overall area of the electrode array illustrated in FIG. 11 is maintained and an area ratio occupied by a plurality of unit (or individual) electrodes is variously changed, and FIG. 13 is a graph illustrating a correlation between an area ratio and an average intensity of an electric field applied to a region-of-interest (ROI) when an electric field is applied using electrode arrays having different area ratios illustrated in FIG. 12.

Referring to FIGS. 11 to 13, it can be seen that the area ratio of the unit electrode should be 30% or more in order to transmit an electric field larger than 1 V/cm to the region-of-interest (ROI).

Considering the above, the use of an electrode array composed of a plurality of unit electrodes during electrical therapy is more practical and reasonable in various aspects than the use of a single flat panel electrode. Specifically, it has the advantage that it is easy to attach an electrode to the curved portion and various side effects can be prevented in advance, as well. In addition, in order to optimize the electric field transmitted to the region-of-interest (ROI) in the body by using the electrode array, it may be understood that the ratio of the area occupied by the unit electrodes to the overall area and shape of the electrode array and the overall area of the electrode array should be set in consideration of the size, shape and depth of the region-of-interest.

Figure 15:
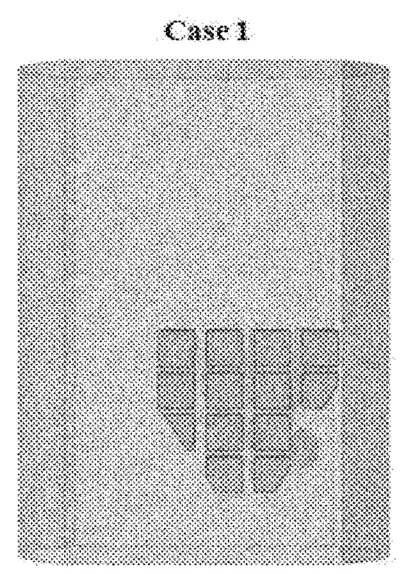
FIG. 15 is a diagram illustrating an example in which a ratio of the overall area, shape, and area of a unit electrode of an electrode array is variously changed in consideration of the shape, size, and internal depth of the region-of-interest (ROI) illustrated in FIG. 14 and an example in which the ratio is applied without change.
Figure 15:
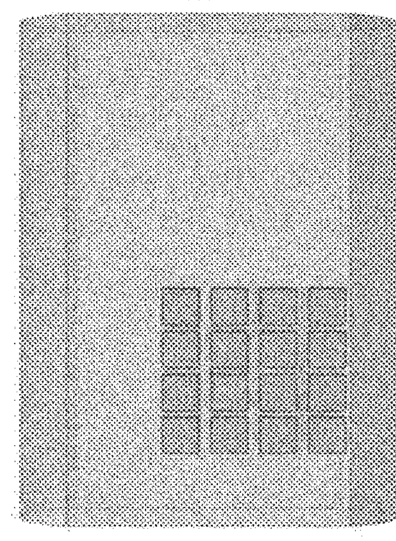
Figure 15:
Figure 15:
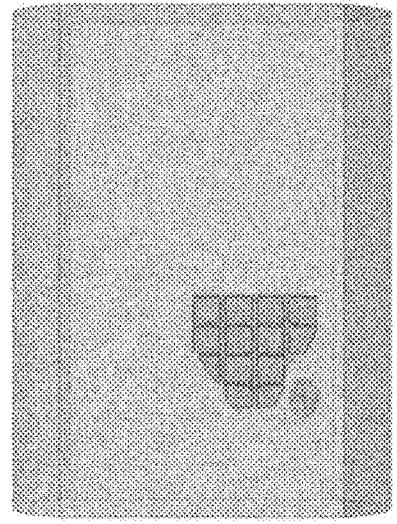
Figure 15:
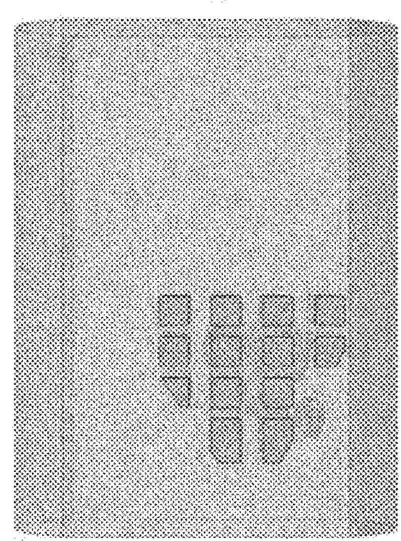
Figures 16, 17:
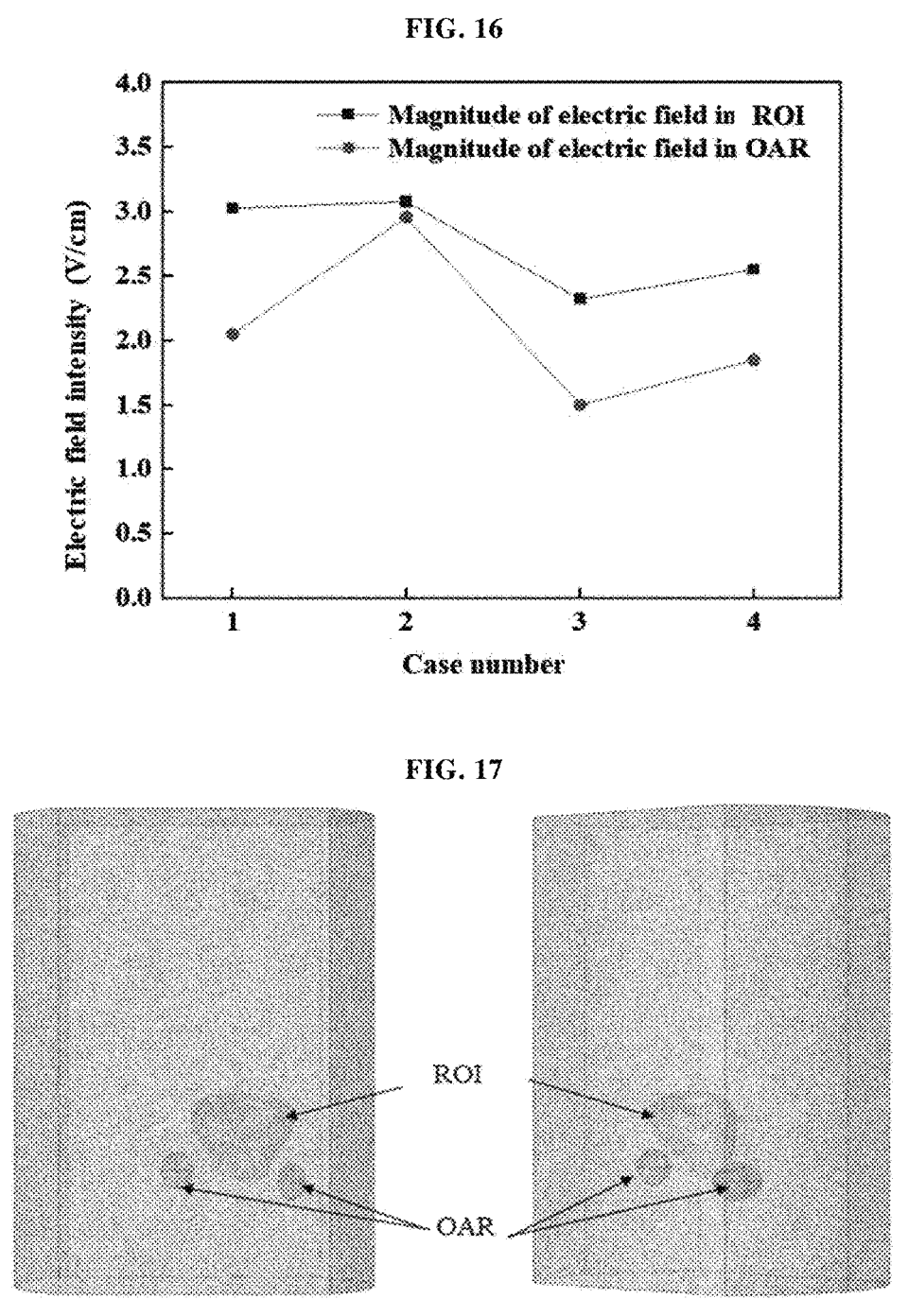

FIG. 14 is a diagram illustrating an example in which a region-of-interest (ROI) and an critical organ are assumed in a human body model phantom according to an embodiment of the present invention, FIG. 15 is a diagram illustrating an example in which a ratio of the overall area, shape, and area of a unit electrode of an electrode array is variously changed in consideration of the shape, size, and internal depth of the region-of-interest (ROI) illustrated in FIG. 14 and an example in which the ratio is applied without change, and FIG. 16 is a graph illustrating the intensity of an electric field applied to the region-of-interest (ROI) and the critical organ with respect to each case illustrated in FIG. 15.

Referring to FIGS. 14 to 16, Case 2 illustrates a case of applying an electrode array without changing the features of electrode array, Cases 1 and 4 illustrate a case of differently setting an area ratio of a unit electrode while changing the shape of the electrode array according to the shape of the ROI, and Case 3 illustrates a case of changing the overall area of the electrode array according to the size of the ROI.

In case 2, there is no significant difference in the intensity of the electric field applied to the region-of-interest (ROI) and the critical organ, but in case 1, case 3, and case 4, it can be seen that the intensity of the electric field applied to the critical organ can be greatly reduced compared to the region-of-interest. In addition, it can be seen that when the area ratio of the unit electrode is relatively large as in case 1, a larger electric field may be transmitted to the region-of-interest, and when the overall area of the electrode array is changed to match the size of the region-of-interest (ROI) as in Case 3, the electric field applied to the critical organ may be minimized.

Figure 18:
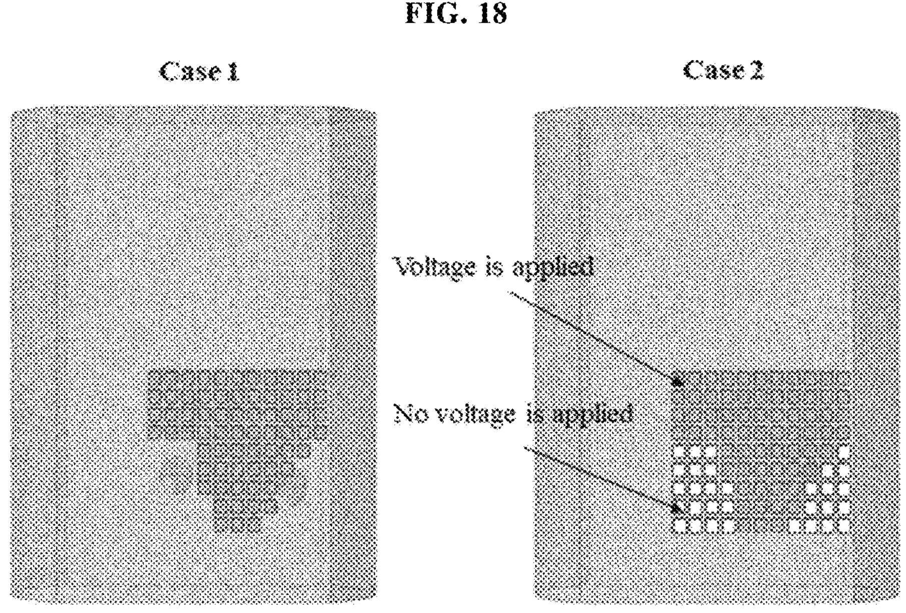
FIG. 18 is a diagram illustrating a comparison between a customized electrode array considering the shape, size, and internal depth of the region-of-interest (ROI) illustrated in FIG. 17 and an electrode array optimized by selectively applying a voltage in consideration of the region-of-interest (ROI) using an electrode array template having a predetermined structure.
Figure 19:
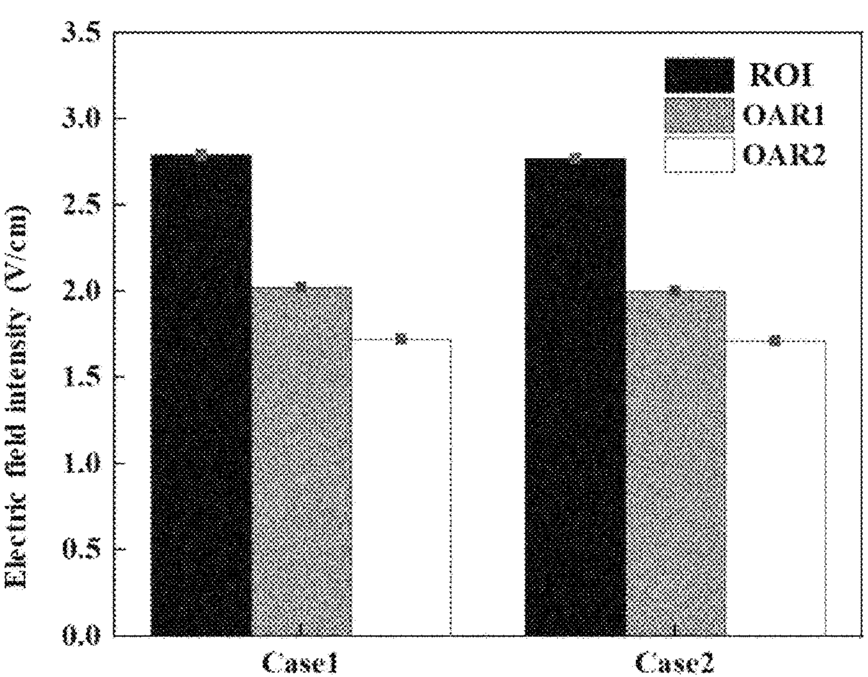
FIG. 19 is a graph illustrating the comparison between the intensities of electric fields applied to the region-of-interest (ROI) and the critical organ for each case illustrated in FIG. 18.

FIG. 17 is a diagram illustrating an example in which a region-of-interest (ROI) and a critical organ are assumed in a human body phantom according to another embodiment of the present invention, FIG. 18 is a diagram illustrating a comparison between a customized electrode array considering the shape, size, and internal depth of the region-of-interest (ROI) illustrated in FIG. 17 and an electrode array optimized by selectively applying a voltage in consideration of the region-of-interest (ROI) using an electrode array template having a predetermined structure, and FIG. 19 is a graph illustrating the comparison between the intensities of electric fields applied to the region-of-interest (ROI) and the critical organ for each case illustrated in FIG. 18.

Referring to FIGS. 17 to 19, when an electrode array having a shape similar to that of the ROI is used and when a voltage is applied only to a unit electrode corresponding to a position of the ROI in an electrode array template, it can be seen that the intensity of an electric field applied to the ROI is 2.79 and 2.77 V/cm, respectively, which are very similar values. In addition, it can be seen that the intensities of the electric fields applied to the first and second critical organs have similar values in the above-described two cases.

Based on these results, it can be seen that the electrode array structure can be optimized by selectively applying a voltage in consideration of the ROI using an electrode array having a shape similar to the shape of the ROI or an electrode array template having a predetermined structure in order to apply an optimized electric field to the human body.

Figure 20:
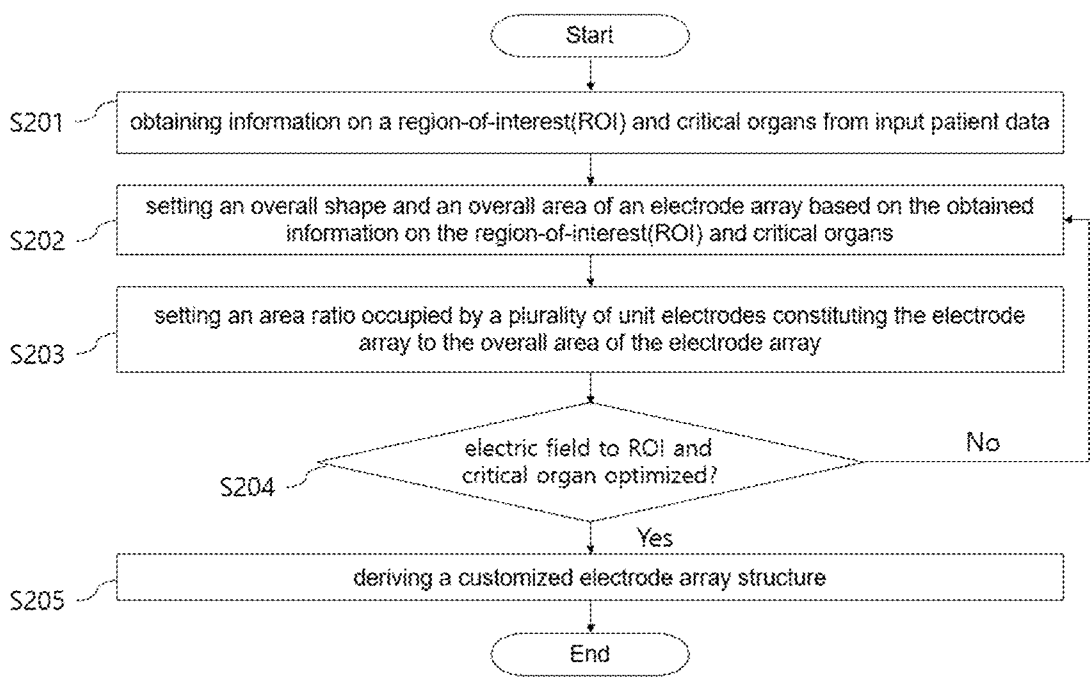
FIG. 20 is a flowchart of a method of optimizing an electrode array structure in electrotherapy according to an embodiment of the present invention.

FIG. 20 is a flowchart of a method of optimizing an electrode array structure in electrotherapy according to an embodiment of the present invention.

Referring to FIG. 20, a region-of-interest (ROI) and critical organ information may be obtained from input patient data (S201).

According to an embodiment, the patient data may be a medical image (e.g., 3D medical image data) of a patient, and in this case, the region-of-interest (ROI) (e.g., a lesion to be treated) and an critical organ region located near the region-of-interest (ROI) may be divided from the medical image of the patient to obtain the region-of-interest (ROI) and critical organ information. Here, the ROI information may include size, shape, and body depth information of the ROI, and the critical organ information may include shape and position information of the critical organ.

According to another embodiment, the region-of-interest (ROI) and critical organ information may be directly received from an external system or terminal and utilized.

Then, the entire shape and overall area of the electrode array may be set based on the obtained region-of-interest (ROI) information (S202).

According to an embodiment, the overall shape of the electrode array may be set based on the shape of the region-of-interest (ROI) from the viewpoint of the skin to which the electrode is attached (that is, from the viewpoint of the electrode). In this case, pairs of electrode arrays may be attached to face each other with respect to a region-of-interest, and at least one of the pairs of electrode arrays may be set in shape in consideration of shapes and positions of critical organs located around the electrode array as well as shapes of the region-of-interest (ROI) from an electrode viewpoint. In addition, the overall area of the electrode array may be set to a critical area, which is an area where the average strength of the electric field transmitted to the region-of-interest (ROI) starts to be constant, based on the set entire shape of the electrode array. In this case, the saturation critical area may be calculated by additionally considering not only the size of the region-of-interest (ROI) but also the depth in the body.

According to another embodiment, the electrode array template having a predetermined structure may be used, and the entire shape and area of the electrode array may be optimized by selectively applying a voltage to only the unit electrode corresponding to the entire shape of the electrode array set as described above.

Thereafter, a ratio of an area occupied by a plurality of unit electrodes to the total area of the electrode array may be set (S203).

According to an embodiment, the area ratio may be set so that the intensity of the electric field is equal to or greater than the intensity of the electric field capable of maximizing the clinical treatment effect, with reference to the correlation information between the area ratio occupied by the plurality of unit electrodes in the total area of the pre-stored electrode array and the intensity of the electric field transferred to the region-of-interest.

The above-described steps S202 and S203 may be repeatedly performed until the region-of-interest (ROI) and the electric field transmitted to the critical organ are optimized (S204).

According to an embodiment, the electric field simulator may simulate the electric field transmitted to the region-of-interest (ROI) and the critical organ according to the variables of the electrode array set in S202 and S203, and the operations S202 and S203 may be repeatedly performed until the electric field transmitted to the region-of-interest (ROI) and the critical organ satisfies a predetermined reference based on the simulation result.

Thereafter, a customized electrode array structure in which the electric field is optimized may be derived (S205).

According to an embodiment, a structure of a customized electrode array may be derived, which depends on variables of the electrode array satisfying a predetermined criterion, that is, an overall shape and an overall area of the electrode array, and an area ratio occupied by a plurality of unit electrodes in the overall area of the electrode array.

In addition, the electrode array structure may be optimized by selectively applying a voltage in consideration of the ROI using an electrode array manufactured according to the customized electrode array structure derived as described above or an electrode array template having a predetermined structure.

Figure 21:
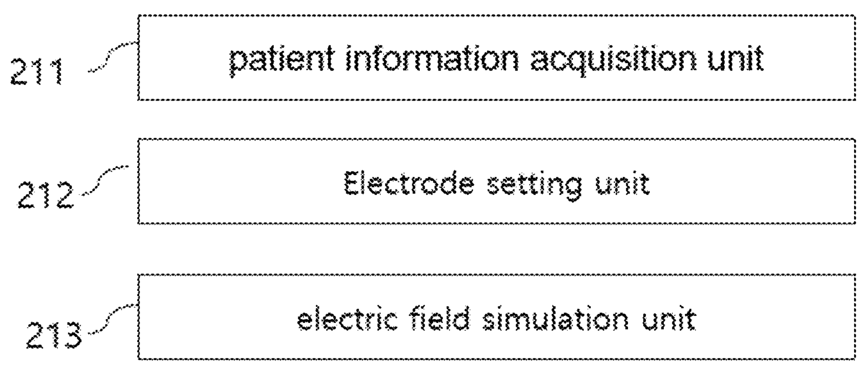
FIG. 21 is a configuration diagram of a system for optimizing an electrode array structure in electrotherapy according to another embodiment of the present invention.

The method for optimizing an electrode array structure in electrotherapy according to an embodiment of the present invention described above with reference to FIG. 20 may be performed by a processing device, for example, an electrode array structure optimization system in electrotherapy illustrated in FIG. 21.

FIG. 21 is a configuration diagram of a system for optimizing an electrode array structure in electrotherapy according to another embodiment of the present invention.

Referring to FIG. 21, a system 210 for optimizing an electrode array structure in electrotherapy according to another embodiment of the present invention may include a patient information acquisition unit 211, an electrode array structure setting unit 212, and an electric field simulation unit 213.

The patient information acquisition unit 211 may acquire a region-of-interest (ROI) and critical organ information from the input patient data.

The electrode array structure setting unit 212 may set variables of the electrode array that determine the electrode array structure based on the region-of-interest (ROI) and the critical organ information acquired by the patient information acquisition unit 211, that is, a ratio of an entire shape and an overall area of the electrode array to an area occupied by a plurality of unit electrodes constituting the electrode array in the overall area of the electrode array, and derive a customized electrode array structure in which an electric field transmitted to the region-of-interest (ROI) and the critical organ is optimized based on a simulation result of the electric field simulation unit 213 to be described later.

The electric field simulation unit 213 may simulate the electric field transmitted to the region-of-interest (ROI) and the critical organ according to the variables of the electrode array set by the electrode array structure setting unit 212.

The details performed by the patient information acquisition unit 211, the electrode array structure setting unit 212, and the electric field simulation unit 213 are the same as those described above with reference to FIG. 20, and thus a repeated description thereof will be omitted.

The present invention is not limited to the above-described embodiments and the accompanying drawings. It will be apparent to those skilled in the art to which the present disclosure pertains that the elements according to the present disclosure may be substituted, modified, and changed without departing from the spirit of the present disclosure.

The invention claimed is:

1. A method of optimizing an electrode array structure in electrotherapy, the method comprising:
- obtaining information on a region-of-interest (ROI) and critical organs from input patient data;
- setting an overall shape and an overall area of an electrode array based on the obtained information on the region-of-interest (ROI) and critical organs;
- setting an area ratio occupied by a plurality of unit electrodes constituting the electrode array to the overall area of the electrode array;
- repeatedly performing the setting of the overall shape and the overall area and/or the setting of the area ratio until an electric field transmitted to the region-of-interest (ROI) and the critical organs is optimized; and
- deriving a customized electrode array structure in which the electric field is optimized,
- wherein the overall area of the electrode array is a saturation critical area, which is an area where the average intensity of the electric field transmitted to the region-of-interest (ROI) starts to be constant, based on the set overall shape of the electrode array.

2. The method of claim 1, wherein obtaining information on a region-of-interest (ROI) and critical organs comprises dividing the region-of-interest (ROI) and the critical organ from the input medical image of the patient.

3. The method of claim 2, wherein the information on a region-of-interest (ROI) contains information about a size, a shape, and an internal depth of the body of the patient, and the information on critical organ contains information about a shape and a location of the critical organ.

4. The method of claim 3, wherein the setting of the overall shape and the overall area comprises setting the overall shape of the electrode array based on a shape of a region-of-interest (ROI) from a viewpoint of the skin to which the electrode is attached.

5. The method of claim 4, wherein the setting of the overall shape and the overall area comprises setting the overall shape of the electrode array by additionally considering the shape and position of the critical organ.

6. The method of claim 1, wherein the saturation critical area is calculated based on the following Equation:

$$\text{A saturation critical area} = \left(\text{a minimum value among } A \text{ values making } \frac{dI}{dA} \cong 0\right),$$

where I is average intensity of an electric field transmitted to the region-of-interest, and A is an entire area of the electrode array as a feature.

7. The method of claim 6, wherein the saturation critical area is calculated by considering the size of the region-of-interest (ROI) and the depth of the body.

8. The method of claim 1, wherein the area ratio is set so that the intensity of the electric field is equal to or greater than the intensity of the electric field that can maximize the clinical treatment effect with reference to correlation information between the area ratio of the electrode array and the intensity of the electric field transferred to the region-of-interest.

9. The method of claim 1, wherein the repeatedly performing the setting of the overall shape, the overall area and the setting of the area ratio comprises
- simulating an electric field transmitted to the region-of-interest (ROI) and the critical organ according to the ratio and the overall shape previously set, and
- repeatedly changing any of the overall shape, the overall area and the setting of the area ratio until the electric field transmitted to the region-of-interest (ROI) and the critical organ satisfies a predetermined criterion from the simulation results.

10. The method of claim 1, wherein deriving a customized electrode array structure can be implemented by customizing electrode array structure or by selectively applying a voltage to only a unit electrode corresponding to the overall shape of the electrode array while using an electrode array template having a predetermined structure.

* * * * *